United States Patent [19]

Takaki

[11] Patent Number: 5,505,200
[45] Date of Patent: Apr. 9, 1996

[54] BIOMEDICAL CONDUCTOR CONTAINING INORGANIC OXIDES AND BIOMEDICAL ELECTRODES PREPARED THEREFROM

[75] Inventor: Shunsuke Takaki, Sagamihara, Japan

[73] Assignee: Minnesota Mining and Manufacturing, St. Paul, Minn.

[21] Appl. No.: 189,082

[22] Filed: Jan. 28, 1994

[51] Int. Cl.[6] ................................................ A61B 5/04
[52] U.S. Cl. ........................................................ 128/640
[58] Field of Search ........................... 128/639, 640, 128/641; 607/149, 152, 153; 439/87; 174/126.1, 126.2

[56] References Cited

U.S. PATENT DOCUMENTS

| | | | |
|---|---|---|---|
| 3,500,823 | 11/1967 | Richardson et al. | 128/639 |
| 3,976,055 | 8/1976 | Monter et al. | 128/2.06 E |
| 4,172,183 | 10/1979 | Rüetschi | 429/128 |
| 4,270,543 | 6/1981 | Tabuchi et al. | 128/639 |
| 4,365,634 | 12/1982 | Bolt et al. | 607/152 |
| 4,377,170 | 3/1983 | Carim | 128/639 |
| 4,406,827 | 9/1983 | Carim | 128/639 |
| 4,466,470 | 8/1984 | Bruder | 141/1.1 |
| 4,777,954 | 10/1988 | Keusch et al. | 607/152 |
| 4,800,883 | 9/1989 | Shigeta et al. | 607/153 |
| 4,846,185 | 7/1989 | Carim | 128/641 |
| 4,848,353 | 7/1989 | Engel | 607/152 |
| 4,852,571 | 8/1989 | Gadsby et al. | 128/640 |
| 4,855,077 | 8/1989 | Shikinami et al. | 252/518 |
| 4,860,754 | 8/1989 | Shovik et al. | 128/640 |
| 4,927,408 | 5/1990 | Hook et al. | 607/152 |
| 5,012,810 | 5/1991 | Strand et al. | 128/640 |
| 5,042,144 | 8/1991 | Shimoda et al. | 128/641 |
| 5,124,076 | 6/1992 | Smuckle | 128/640 |
| 5,133,356 | 7/1992 | Bryan et al. | 128/640 |
| 5,215,087 | 6/1993 | Anderson et al. | 128/640 |
| 5,276,079 | 1/1994 | Duan et al. | 524/386 |
| 5,337,748 | 8/1994 | McAdams et al. | 607/149 |
| 5,352,315 | 10/1994 | Cahn et al. | 607/149 |

FOREIGN PATENT DOCUMENTS

| | | |
|---|---|---|
| 0542294A1 | 5/1993 | European Pat. Off. . |
| 0585933A2 | 3/1994 | European Pat. Off. . |
| 0160439 | 10/1982 | Japan ........................ 128/641 |

OTHER PUBLICATIONS

Nencini et al., "Manganese Dioxide Electrodes For Stimulation and Recording", *Medical and Biological Engineering* vol. 6, pp. 193–197 (1968).

Nencini et al., "Manganese Dioxide Depolarizer For Biomedical Electrodes", *Medical and Biological Engineering*, vol. 8, pp. 137–143 (1970).

*Primary Examiner*—Lee S. Cohen
*Assistant Examiner*—Bria M. Green
*Attorney, Agent, or Firm*—Gary L. Griswold; Walter N. Kirn; John H. Hornickel

[57] ABSTRACT

A biomedical electrical conductor having a thin, conformable layer of an inorganic oxide of low polarizability is disclosed. The inorganic oxide can be a manganese oxide, preferably manganese dioxide. The biomedical electrical conductor as a multi-layered composite also is disclosed, using the inorganic oxide layer in mechanical and electrical association with an electrically conductive component which is mechanically in association with a nonconductive polymeric film. The composite forms an essentially x-ray transparent, flexible conductor of low polarizability. Biomedical electrodes using the biomedical electrical conductor and methods of making and using the conductors and the electrodes are also disclosed.

18 Claims, 1 Drawing Sheet

BIOMEDICAL CONDUCTOR CONTAINING INORGANIC OXIDES AND BIOMEDICAL ELECTRODES PREPARED THEREFROM

FIELD OF THE INVENTION

This invention relates to electrical conductors containing inorganic oxides for use in biomedical electrodes.

BACKGROUND OF THE INVENTION

Modern medicine uses many diagnostic procedures where electrical signals or currents are received from a mammalian patient's body. Nonlimiting examples of diagnostic procedures include electrocardiographic (ECG or EKG) diagnosis or monitoring of electrical wave patterns of a mammalian heart, irrespective of duration or circumstance. The point of contact between medical equipment used in these procedures and the skin of the patient is usually some sort of biomedical electrode. Such an electrode typically includes a conductor which must be connected electrically to the equipment, and a conductive medium adhered to or otherwise contacting skin of a patient.

Among diagnostic procedures using biomedical electrodes are monitors of electrical output from body functions, such as electrocardiographs (ECG) for monitoring heart activity and for diagnosing heart abnormalities.

For each diagnostic procedure, at least one biomedical electrode having an ionically-conductive medium containing an electrolyte is adhered to or otherwise contacting skin at a location of interest and also electrically connected to electrical diagnostic equipment. A critical component of the biomedical electrode is the electrical conductor in electrical communication with the ionically-conductive medium and the electrical diagnostic equipment.

Electrical conductors require excellent electrical conductivity and minimal electrical resistance for biomedical electrodes, especially when faint electrical signals are received from the patient. For this reason, metals or carbon (especially graphite) are used. Among metals, silver is preferred because of its optimal conductivity. But biomedical electrodes which monitor a patient's conditions must be able to withstand the polarizing effects of a defibrillation procedure for a heart. For this reason, a metal halide, such as silver chloride, is preferably used with a metal conductor, such as silver, to create a depolarizable electrical conductor in biomedical electrodes which can monitor a heart.

There are two principal difficulties with a biomedical electrode containing silver/silver chloride: expense of silver and x-ray detection of metallic silver.

Others have attempted to reduce the cost of silver in biomedical electrodes by using graphite or other galvanically inactive materials in association with silver particles in silver/silver chloride layers. See, for example, U.S. Pat. Nos. 3,976,055 (Monter et al.) and 4,852,571 (Gadsby et al.).

Manganese dioxide has been investigated for use with biomedical electrodes as a nonpolarizable material when prepared as a thick pellet and placed in association with graphite. See Nencini et al., "Manganese Dioxide Electrodes For Stimulation and Recording" in *Medical and Biological Engineering* Vol. 6, pp. 193–197 (1968) and Nencini et al., "Manganese Dioxide Depolarizer For Biomedical Electrodes" in *Medical and Biological Engineering*, Vol. 8, pp. 137–143 (1970). But no biomedical electrode is known to have been constructed using $MnO_2$ in a manner that permits the electrode to conform to the contours of the skin of a patient.

Other uses of manganese dioxide in electrical apparatus include uses in batteries where electrical energy is gathered and stored for later release. See, for example, U.S. Pat. No. 4,466,470 (Alan et al.).

SUMMARY OF THE INVENTION

The present invention provides a biomedical electrical conductor comprising a thin, conformable layer of an inorganic oxide of low polarizability contacting an electrically conductive component which is capable of becoming in electrical communication with diagnostic equipment. The present invention also provides the use of that biomedical electrical conductor in a biomedical electrode.

"Low polarizability" means that the inorganic oxide is capable of retaining an equilibrium potential after being exposed to a high voltage of electricity used to defibrillate the heart of a patient.

The thin layer of the inorganic oxide permits the biomedical electrical conductor to have a flexible structure and a low profile. Thus, the conductor is capable of bending to conform to the contours of skin to which a biomedical electrode using the conductor can contact.

"Thin" means that the layer of inorganic oxide is less than about 100 μm thick.

"Conformable" means that the layer of inorganic oxide can flex and bend to permit a biomedical electrode containing the layer to contact a sufficient area of skin of a patient to permit accurate and precise reception of biomedical electrical signals emanating from the patient in the location of electrode contact.

Of possible inorganic oxides, various oxides of manganese are preferred. Oxides of manganese, particularly manganese dioxide in its various commercially available forms, are suitable for the rapid reactions which are required to maintain low polarizability of an electrical conductor within a biomedical electrode on a patient after an electrical defibrillation procedure of that patient is completed.

As recognized by Nencini identified above, little is known how oxides of manganese operate to maintain low polarizability. While not being limited to a particular theory, manganese dioxide in commercially available forms are believed to have oxides of manganese having more than one oxidation state, such that low polarizability for the electrical conductor is achieved by either reduction reactions or oxidation reactions of the various oxides of manganese present in commercially available manganese dioxide. These reduction/oxidation (REDOX) reactions are rapid and permit maintenance of low polarizability of the electrical conductor after being exposed to a high voltage of electricity used to defibrillate the heart of a patient.

The present invention also achieves a biomedical electrode comprising a biomedical electrical conductor described herein. The biomedical electrode comprises a biomedical electrical conductor described herein and an ionically-conductive medium contacting the conductor and also contacting the skin of a patient.

A feature of the present invention is that, when compared to a silver/silver chloride biomedical electrical conductor, the biomedical electrical conductor of the present invention is essentially x-ray transparent.

Another feature of the present invention is that, when compared to a silver/silver chloride biomedical electrical conductor, the biomedical electrical conductor of the present invention is relatively inexpensive because of the difference in material cost of manganese dioxide compared with silver.

An advantage of the present invention is that a biomedical electrical conductor described herein has all of the properties of preferred silver/silver chloride electrodes with the benefits of essentially x-ray transparency and low materials cost. For a greater appreciation of the invention, embodiments of the invention are described in relation to the drawings.

EMBODIMENTS OF THE INVENTION

Biomedical Electrical Conductor

A biomedical electrical conductor of the present invention comprises a thin, conformable depolarizing layer of an inorganic oxide contacting an electrically conductive component which capable of becoming in electrical communication with diagnostic equipment.

Nonlimiting examples of electrically conductive components include mushroom-shaped snaps, eyelets, posts, thin layers on substrates, and electrically conductive particles intermixed in the thin, conformable depolarizing layer of inorganic oxide.

Preferably, the electrically conductive component is a layer in contact with the thin, conformable depolarizing layer. Preferably, the layer is flexible, conformable, and essentially x-ray transparent.

Nonlimiting examples of materials suitable for the electrically conductive component include intrinsically conductive polymers and various forms of carbon, especially graphite, such as carbon-containing inks, carbon-based fibers, carbon-loaded woven and nonwoven webs, carbon-loaded membranes, and other composites. Graphite is preferred, especially when applied in the form of a graphite ink to a nonconductive, thin, flexible polymer film (e.g., a polyester film).

Alternatively, particles of the electrically conductive component can be intermixed with particles of the inorganic oxides to form a blended, thin, conformable, essentially x-ray transparent layer.

The thin layer of inorganic oxide provides a depolarizing layer as a part of the biomedical electrical conductor and preferably covers the area of contact between an electrically conductive layer and an ionically conductive medium in a biomedical electrode.

The thin layer of inorganic oxide either can be a gel containing the inorganic oxide covering the electrically conductive layer or can be a thin film coated on the electrically conductive layer using a binder.

Of possible inorganic oxides, manganese dioxide is readily available commercially in a variety of crystalline forms, has low polarizability, and is inexpensively priced compared with silver.

Because commercially available manganese dioxide can oxidize other compositions, depending on the oxidation state(s) of the oxides of manganese present in commercially available manganese dioxide, some care must be taken in the selection of compositions contacting it to avoid undesirable decomposition.

Graphite is an excellent choice as an electrically conductive component for contact with manganese dioxide. The graphite can contact oxides of manganese as either particles to be intermixed in the thin depolarizing layer or formed as a separate electrically conductive layer which contacts the thin depolarizing layer.

Graphite has a high electrical conductivity, is x-ray transparent, and is inert to oxidative effects of oxides of manganese.

To form a thin, conformable, continuous film of depolarizing layer on an electrically conductive layer, particles of oxides of manganese require a binder and can be applied as an ink to the electrically conductive layer. In this manner, the thin, conformable depolarizing layer is sandwiched between the electrically conductive layer and the ionically conductive medium.

Alternatively, particles of oxides of manganese and particles of electrically conductive component can be intermixed with a binder and applied as an ink to an electrically nonconductive substrate in a blended layer to provide a thin, conformable, electrically conductive and depolarizing layer.

A binder relatively resistant to oxidation by inorganic oxides, especially oxides of manganese, can be a water-soluble polymer. Nonlimiting examples include celluloses such as methyl cellulose, polyethylene oxide, poly(vinyl alcohol), and poly(N-vinyl lactam), such as poly(N-vinyl-2-pyrrolidone). Of these polymers, methyl cellulose with a limited number of unreacted hydroxy groups thereon (i.e., less than fully-hydroxy-terminated) and poly(vinyl alcohol) are preferred.

The particles of inorganic oxide can range in size from about 0.1 µm to about 50 µm, and preferably about 1 µm.

When the inorganic oxide are oxides of manganese, the crystalline structure can be any structure that result in a low polarizability. Nonlimiting examples include $\alpha$-$MnO_2$, $\beta$-$MnO_2$, and $\gamma$-$MnO_2$, with $\gamma$-$MnO_2$ being preferred.

The solids content of inorganic oxide in the thin, conformable depolarizing layer can range in an amount from about 10 to about 99.99 weight percent of the layer, preferably about 40 to about 99 weight percent, and most preferably about 97 weight percent. The binder constitutes the balance of the thin, conformable depolarizing layer when the layer is constructed to contact a separate, electrically conductive layer.

In the embodiment where particles of inorganic oxide and electrically conductive component are intermixed to form a blended layer, the solids content of inorganic oxide in the blended layer ranges from about 1 to about 99 weight percent of the layer; the solids content of the electrically conductive component ranges from about 1 to about 99 weight percent of the layer; and binder constitutes the balance of the weight. Preferably, the weight percent of inorganic oxide, electrically conductive component, and binder ranges from about 50 to about 90; from about 10 to about 50; and the balance; respectively.

A volatile liquid is used to dissolve the binder. Particles of inorganic oxide, and optionally also particles of electrically conductive component are mixed in the volatile liquid to form an ink. The volatile liquid is preferably water. After applying the ink, the volatile liquid is evaporated upon coating onto a substrate. In a multi-layer embodiment, the substrate is the electrically conductive layer. In the blended layer embodiment, the substrate is an electrically nonconductive film that serves as a backing for the electrical conductor.

Other components optionally can be included in the ink. To assist the water-soluble polymer bind particles of the manganese dioxide, an inorganic salt, such as calcium chloride or potassium chloride, can be added in an amount ranging from about 0.1 to about 3 weight percent of the solids content of the ink and preferably about 1 weight percent of solids content of the ink. When poly(vinyl alcohol) is used as the binder, calcium chloride acts an ionic crosslinker for poly(vinyl chloride), increasing binding effect.

Also optionally, a commercially available surfactant, such as sorbitan monooleate commercially available from Wako Co. of Tokyo, Japan or polyoxyethylene sorbitan monooleate commercially available also from Wako Co. can be included in the ink up to about 0.5 weight percent of the solids content of the ink but can decrease adhesion of the depolarizing layer to the electrically conductive layer. Preferably, surfactant is not needed for the ink used to prepare the depolarizing layer.

Also optionally, to achieve higher electrical conductivity in the depolarizing layer in the multi-layer embodiment, carbon or graphite particles can be included in the ink in amounts ranging from about 1 to about 90 weight percent of the solids content of the ink.

Also optionally, to increase adhesiveness of the depolarizing layer to the electrically conductive layer, a water phase-acrylic emulsion adhesive can be added in the ink in amounts ranging from about 0 to about 90 weight percent of the ink.

The acrylic emulsion adhesive can be a reaction product of the polymerization of at least one A monomer and at least one B monomer to yield a copolymer having an inherent viscosity of about 1.0 dl/g to about 2.0 dl/g. The A monomer is a polymerizable monomer comprising an acrylate or methacrylate ester of a non-tertiary alcohol or a mixture of non-tertiary alcohols with the alcohols having from 1 to 14 carbon atoms and desirably averaging about 4 to 12 carbon atoms.

The B monomer is an ethylenically unsaturated compound and desirably may be acrylic acid, methacyrlic acid, itaconic acid, acrylamide, methacrylamide, acrylonitrile, methacrylonitrile, vinyl acetate, N-vinyl pyrrolidone, or combinations thereof.

The A monomer is polymerizable and contributes the viscoelastic properties of the pressure sensitive adhesive copolymer. Non-limiting examples of such A monomers include the esters of acrylic acid or methacrylic acid with non-tertiary alkyl alcohol such as 1-butanol, 1-pentanol, 2-pentanol, 3-pentanol, 2-methyl-1-butanol, 1-methyl-1-butanol, 1-methyl-1-pentanol, 2-methyl-1-pentanol, 3-methyl-1-pentanol, 2-ethyl-1-butanol, 2-ethyl-1-hexanol, 3,5,5-trimethyl-1-hexanol, 3-heptanol, 2-octanol, 1-decanol, 1-dodecanol, and the like. Such monomeric acrylic or methacrylic esters are known in the art, and many are commercially available.

The B monomer is an ethylenically unsaturated compound copolymerized with the A monomer to affect the physical properties of the resulting pressure sensitive adhesive copolymer. In general, the presence of the B monomer will reduce the flexibility of the resulting pressure sensitive adhesive copolymer.

Thus, the weight percentages of the A monomer and the B monomer should be balanced in order to provide a pressure sensitive adhesive copolymer having an inherent viscosity of from about 1.0 dl/g to about 2.0 dl/g. The weight percentage ratio of A monomer: B monomer ranges from about 85:15 to about 98:2 and desirably from about 90:10 to 97:3.

Preferably, the adhesive can be a copolymer of isooctyl acrylate and acrylic acid in a weight percentage ratio of about 95:5 and can be prepared according to U.S. Pat. No. RE24,906 (Ulrich).

If electrolytic manganese dioxide is used in the ink, then addition of an alkaline agent to control pH is also needed to get good dispersion stability. For example, potassium hydroxide can be added in an amount of about 1.5 weight percent of the solids content of the ink.

Biomedical Electrodes

Biomedical electrodes employing biomedical electrical conductors of the present invention are useful for monitoring or diagnostic purposes. In its most basic form, a biomedical electrode comprises an ionically conductive medium contacting skin and a means for electrical communication interacting between the ionically conductive medium and electrical diagnostic equipment.

Figures 1, 2:
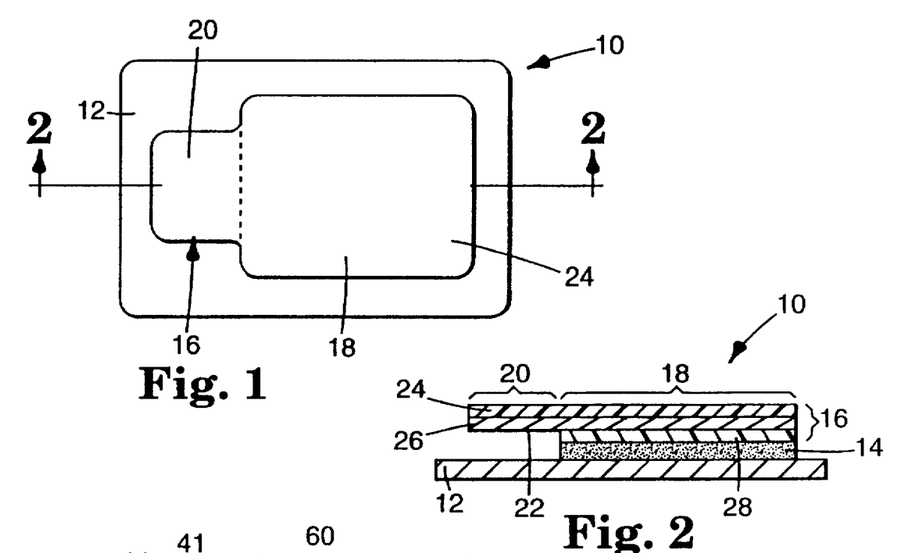
FIG. 1 is a top plan view of a biomedical electrode containing a biomedical electrical conductor of the present invention.
FIG. 2 is a sectional view of the biomedical electrode of FIG. 1.

FIGS. 1 and 2 show a disposable diagnostic electrocardiograph (ECG or EKG) electrode 10 on a release liner 12. Electrode 10 includes a field 14 of a biocompatible, adhesive, ionically conductive medium for contacting skin of a patient upon removal of protective release liner 12. Electrode 10 includes means for electrical communication of the present invention comprising a biomedical electrical conductor 16 having a conductive interface portion 18 contacting field 14 of ionically conductive medium and a tab portion 20 not contacting field 14 of conductive medium for mechanical and electrical contact with electrical equipment (not shown).

In this multi-layer embodiment, conductor 16 is shown in a multi-layered construction of a nonconductive, flexible polymeric film 24, an electrically conductive layer 26, and a thin, conformable depolarizing layer 28. The conductive interface portion 18 of member 16 comprises an electrically conductive layer 26 coated on at least the side of polymeric film 24 facing field 14 of conductive medium and the thin, depolarizing layer 28 coated on the electrically conductive layer 26 and contacting field 14. Because depolarizing is not needed for the mechanical and electrical contact with electrical equipment, depolarizing layer 28 need not extend to tab portion 20.

In the blended layer embodiment, conductor 16 is a multi-layered construction of film 24 with layers 26 and 28 blended together.

It is foreseen that a typical EKG conductor member 16 be thin, flexible, and conformable. Polymeric film 24 typically has a thickness ranging from about 10 μm to about 200 μm, and preferably has a thickness of about 75 μm. Electrically conductive layer 26, as a graphite layer applied from an ink, has a dried thickness ranging from about 1 μm to about 100 μm, and preferably has a thickness of about 12 μm. Depolarizing layer 28, as a manganese dioxide layer applied from an ink, has dried thickness ranging from about 1 μm to about 100 μm, and preferably a thickness of about 50 μm. Layer 26 and layer 28 total in thickness from about 2 to about 200 μm, and preferably about 72 μm, whether in the embodiment of separate layers shown in FIG. 1 or blended together. This cumulative thickness permits the electrical conductor 16 to conformable to contours to skin of a patient.

Presently preferred for polymeric film 24 are a polyester film commercially available as "Mellinex" 505-300, 329, or 339 film from ICI Americas of Hopewell, Va. and a polyester (polyethylene terephthalate) film commercially available as "EMBLET T-100" or "EMBLET T-75" film from Unitika Co. of Osaka, Japan.

Presently preferred for electrically conductive layer 26 is a graphite ink commercially available in Japan as "JEF-120" from Acheson Japan Co. Ltd. of Kobe, Japan. It is believed that this graphite ink has a polyester binder contained therein. This commercial graphite ink is particularly useful when used dissolved in a butylacetate solvent in a mix of about 80 weight percent graphite ink and about 20 weight percent solvent.

A preferred depolarizing layer 28 is a manganese dioxide film comprising 93.2 weight percent of manganese dioxide powder (0.8 μm average particle size) from Johnson Matthey of Mass., USA, 5.8 weight percent of methyl cellulose binder commercially available as "Marpolose EM 4000" from Matsumoto Chemical Co. of Osaka, Japan, and 1.0 weight percent of potassium chloride. An alternate preferred depolarizing layer 28 is a manganese dioxide film comprising about 25.6 weight percent of electrolytic manganese dioxide powder commercially available from Tosoh Co. of Tokyo, Japan, 6.4 weight percent acidic furnace carbon black commercially available from Mitsubishi Chemical Co. of Tokyo, Japan, 28.8 weight percent of methylcellulose binder stock (a 2.3 weight percent solution of methyl cellulose commercially available as "EM 4000" from Matsumoto Chemical Co. of Osaka, Japan, 7.0 weight percent of an acrylic emulsion adhesive comprising about 95 weight percent isooctyl acrylate and about 5 weight percent acrylic acid prepared according to U.S. Pat. No. RE24,906 (Ulrich), alkaline agent of either 9.6 weight percent of KOH or 1.6 weight percent of a 25% aqueous ammonia solution, and 0.13 weight percent of KCl, with the balance being deionized water. The solids content of the ink is about 36%.

To enhance mechanical contact between an electrode clip (not shown) and tab portion 20 of conductor member 16, an adhesively-backed polyethylene tape can be applied to tab portion 20 on the side opposite side 22 having the electrically conductive layer 26. A surgical tape commercially available from 3M Company as "Blenderm" tape can be employed for this purpose.

As stated previously, some care must be taken when selecting an ionically conductive medium for contact with the depolarizing layer 28.

The ionically conductive medium should be resistant to the oxidative effect of the inorganic oxide, especially decomposing effects on hydroxyl group density on terminal groups of ionically-conductive compositions. For the ionically conductive medium 14, ionically-conductive gels and adhesives which are minimally reactive with manganese dioxide are preferred.

Nonlimiting examples of ionically-conductive pressure sensitive adhesive compositions are commercially available as disclosed in U.S. Pat. No. 4,855,077 (Shikinami et al.). Other useful compositions include solid state conductive polymer compositions disclosed in U.S. patent application Ser. No. 07/792,957 and counterpart European Patent Publication 0 542 294 (Uy et al.), ionically conductive pressure sensitive adhesive compositions disclosed in U.S. Pat. No. 5,276,079 (Duan et al.), and ionically conductive polymerized microemulsion pressure sensitive adhesive compositions disclosed in copending, coassigned U.S. patent application Ser. No. 08/188,269, (Dietz et al.) (Attorney Docket 48237USA7A), the disclosures of which are incorporated by reference, except that essentially non-volatile plasticizer present in any of such ionically conductive compositions is preferably a plasticizer which has a higher molecular weight than about 200 or has hydroxyl groups comprising less than about 3 percent of the molecular weight of the plasticizer. It has been found that limiting hydroxyl group content in the plasticizer to less than about 3 percent causes a biomedical electrode 10 to have appropriate aging characteristics during storage of the electrode 10 prior to use.

Nonlimiting examples of plasticizers useful in ionically conductive compositions are polyethylene glycol methyl ether, 550 molecular weight, commercially available under the "Carbowax" brand from Union Carbide Corporation, polyethylene glycol 2000 molecular weight commercially available also under the "Carbowax" brand from Union Carbide Corporation, and tetraethyleneglycol dimethyl ether commercially available under the "Hysolve" brand from Tohou Chemical Co. of Tokyo, Japan. Of these plasticizers, polyethylene glycol methyl ether, 550 molecular weight is preferred.

Another type of diagnostic procedure which can employ a biomedical electrode of the present invention is the longer term monitoring of electrical wave patterns of the heart of a patient to detect patterns of abnormality. Monitoring biomedical electrode structures are disclosed in U.S. Pat. No. 5,012,810 (Strand et al.), U.S. Pat. No. 4,848,353 (Engel), the disclosures of which are incorporated by reference. The biomedical electrical conductor of the present invention can be used as the conductor member in any of the embodiments shown therein, with the depolarizing layer of the present invention covering the pad portion of the conductor member that contacts a field of conductive adhesive but not covering either side of the tab portion of the conductor member that mechanically and electrically contacts a clip leading to the electrical equipment. Preferably, the biomedical electrical conductor of the present invention is used as the conductor member in the biomedical electrode of the embodiment shown in FIGS. 2, 3, and 4 of U.S. Pat. No. 5,012,810.

Figure 3:
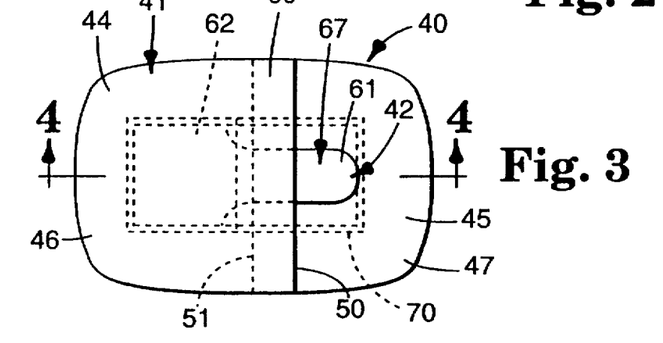
FIG. 3 is a top plan view of another biomedical electrode containing a biomedical electrical conductor of the present invention.
Figure 4:
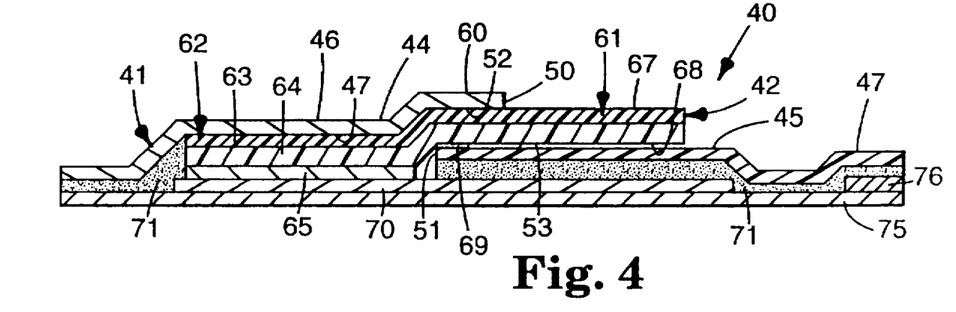
FIG. 4 is a section view of the biomedical electrode of FIG. 3.

FIGS. 3 and 4 substantially correspond to FIGS. 2 and 3, respectively, of U.S. Pat. No. 5,012,810. Electrode 40 includes an insulator construction 41, and a conductor member 42. The insulator construction 41 includes first and second sections 44 and 45 which, together, define opposite sides 46 and 47 of the insulator construction 41. As seen in FIG. 4, each section 44 and 45 includes an elongate edge portion 50 and 51, respectively. The edge portions 50 and 51 each include a border portion 52 and 53, respectively, which comprise a peripheral portion of each section 44 and 45, respectively, and extending along edges 50 and 51, respectively. In that manner, sections 44 and 45 are oriented to extend substantially parallel to one another, with edge portions 50 and 51 overlapping one another such that border portions 52 and 53 overlap. A seam 60 is created between edge portions 50 and 51. "Substantially parallel" does not mean that the sections 44 and 45 are necessarily precisely parallel. They may be out of precise coplanar alignment due, for example, to the thickness of the conductor member 42.

Conductor member 42 is substantially similar to biomedical electrical conductor 16 described above, having a tab portion 61 corresponding to tab portion 20 described above and a pad portion 62 corresponding to conductive interface portion 18 described above. Like biomedical electrical conductor 16, conductor member 42 is a multi-layered construction of a nonconductive, flexible polymeric film 63, an electrically conductive layer 64, and a thin, conformable, depolarizing layer 65. Alternatively, layer 64 and layer 65 can be a blended layer.

The pad portion 62 of member 42 comprises an electrically conductive layer 64 coated on at least the side of polymeric film 63 facing field 70 of conductive adhesive, and the thin, depolarizing layer 65 coated on the electrically conductive layer 64 and contacting field 70. Because depolarizing is not needed for the mechanical and electrical contact with electrical equipment, depolarizing layer 65 does not extend to tab portion 61. Alternatively, layers 64 and 65 can be a blended layer and coated in a single step. Optionally, an adhesively-backed polyethylene tape can be applied to tab portion 61 in the same manner as that for the embodiment of FIGS. 1 and 2, in order to enhance mechanical contact.

In general, electrode 40 is constructed such that tab portion 61 of conductor member 42 projects through seam 60 and over a portion of surface or side 46. As a result, as seen in FIGS. 3 and 4, pad portion 62 of conductor member 42 is positioned on one side 47 of insulator construction 41, and the tab portion 61 of conductor member 42 is positioned on an opposite side 46 of insulator construction 41. It will be understood that except where tab portion 61 extends through seam 60, the seam may be sealed by means of an adhesive or the like.

It may be desired to provide an outside seal over seam 60. Optionally as seen in FIG. 3, this can be accomplished, by placement of a strip 66 of adhesive tape or the like in overlap of seam 60, and partly extending over tab portion 61, transversely to a longitudinal extension thereof. It is also desirable to place an adhesive positioned between surface 47 and upper surface 67 of tab portion 61 contacting section 44. Alternatively, as seen in FIG. 4, lower surface 68 of tab portion 61 is shown adhered in position to section 45, by means of double-stick tape strip 69. That is, adhesion in FIG. 4 between the tab portion 61 and section 45 is by means of adhesive 69 underneath tab portion 61, rather than on top as shown in FIG. 3.

In FIG. 4, a field 70 of conductive adhesive is shown positioned generally underneath conductive member 42. It will be understood that in general the field 70 of conductive adhesive will be surrounded by a field 71 of skin adhesive also applied to insulator construction 41 the side thereof having pad portion 62 thereon.

In FIG. 4, a layer of release liner 75 is shown positioned against that side of electrode 40 which has skin adhesive 71, conductive adhesive 70 and pad portion 62 thereon. Optionally as shown in FIG. 4, a spacer 76 or tab 76 can be positioned between release liner 75 and a portion of insulator construction 41, to facilitate the separation.

A variety of release liners 75 may be utilized; for example, a liner comprising a polymer such as a polyester or polypropylene material, coated with a silicone release type coating which is readily separable from the skin adhesive and conductive adhesive.

A variety of materials may be utilized to form the sections 44 and 45 of the insulator construction 41. In general, a flexible material is preferred which will be comfortable to the user, and is relatively strong and thin. Preferred materials are polymer foams, especially polyethylene foams, nonwoven pads, especially polyester non-wovens, various types of paper, and transparent films. Nonlimiting examples of transparent films include polyester film such as a 0.05 mm polyester film commercially available as "Mellinex" polyester film from ICI Americas, Hopewell, Va. having a thickness of 0.05 mm.

The most preferred materials are non-woven pads made from melt blown polyurethane fibre, which exhibit exceptional flexibility, stretch recovery and breathability. Melt blown polyurethane materials usable in insulator construction 41 in electrodes according to the present invention are generally described in U.S. Pat. No. 5,230,701 (Meyer et al.) incorporated herein by reference.

Preferably the insulator construction has a skin adhesive on its surface contacting the remainder of the electrode 40.

Preferred web materials (melt blown polyurethanes) for use in insulator construction 41 have a web basis weight of about 60–140 $g/m^2$ (preferably about 120 $g/m^2$). Such materials have an appropriate tensile strength and moisture vapor transmission rate. A preferred moisture vapor transmission rate is about 500–3000 grams water/$m^2$/24 hours (preferably 500–1500 grams water/$m^2$/24 hours) when tested according to ASTM E96-80 at 21° C. and 50% relative humidity. An advantage to such materials is that webs formed from them can be made which exhibit good elasticity and stretch recovery. This means that the electrode can stretch well, in all directions, with movement of the subject, without loss of electrode integrity and/or failure of the seal provided by the skin adhesive. Material with a stretch recovery of at least about 85%, in all directions, after stretch of 50% is preferred.

It will be understood that a variety of dimensions may be utilized for the biomedical electrode disclosed herein. Generally an insulator construction of about 3.5–4.5 cm by 5.5–10 cm will be quite suitable for typical foreseen applications. A thickness of about 200 to 600 μm provides for adequate strength and a desired low relief or profile, in typical applications.

It will also be understood that a variety of materials may be utilized as the skin adhesive. Typically, acrylate ester adhesives will be preferred. Acrylate ester copolymer adhesives are particularly preferred. Such material are generally described in U.S. Pat. Nos. 2,973,826; Re 24,906; Re 33,353; 3,389,827; 4,112,213; 4,310,509; 4,323,557; 4,732, 808; 4,917,928; 4,917,929; and European Patent Publication 0 051 935, all incorporated herein by reference.

In particular, an adhesive copolymer having from about 95 to about 97 weight percent iso-octyl acrylate and from about 5 to about 3 percent acrylamide and having an inherent viscosity of 1.1–1.25 dl/g is presently preferred.

Adhesive useful as for adhesive 69 can be any of the acrylate ester adhesives described above in double stick tape form. A presently preferred adhesive is the same adhesive as presently preferred for the skin adhesive except having an inherent viscosity of about 1.3–1.45 dl/g.

For the field 70 of conductive adhesive, conductive adhesives such as those described above as useful for field 14 of conductive medium are preferred.

It will be understood that the dimensions of the various layers, and their conformation during association, are shown somewhat exaggerated in FIG. 4, to facilitate an understanding of the construction. In general, an overall substantially flat appearance with only a very minor "s" type bend in the conductive member 42 is accommodated by the arrangement, despite the multi-layered construction of member 42.

Other examples of biomedical electrodes which can use the present invention as biomedical electrical conductors include electrodes disclosed in U.S. Pat. Nos. 4,527,087; 4,539,996; 4,554,924; 4,848,353 (all Engel); 4,846,185 (Carim); 4,771,713 (Roberts); 4,715,382 (Strand); 5,133,356 (Bryan et al.); and U.S. Pat. No. 5,215,087 (Anderson et al.); the disclosures of which are incorporated by reference herein. Methods of making such electrodes are disclosed in such patents, except that the biomedical electrical conductor of the present invention can be substituted for the various means of electrical communication disclosed in such patents.

Among these various electrode constructions is an electrode construction particularly preferred as that shown in FIGS. 1-2 of U.S. Pat. No. 4,539,996 (Engel) in which backing 13 having electrical conductor 12 is replaced by the biomedical electrical conductor of the present invention.

Electrodes disclosed in U.S. Pat. Nos. 4,539,996; 4,848,353; 5,012,810; and 5,133,356 are preferred.

In some instances, biomedical electrical conductor can be an electrically conductive tab extending from the periphery of the biomedical electrodes such as that seen in U.S. Pat. No. 4,848,353 or can be a conductor member extending through a slit or seam in a insulating backing member, such as that seen in U.S. Pat. No. 5,012,810. Otherwise, the means for electrical communication can be an eyelet or other snap-type connector such as that disclosed in U.S. Pat. No. 4,846,185 with the depolarizing layer coated on a graphite coated snap electrode. Alternatively, an electrically conductive tab such as that seen in U.S. Pat. No. 5,012,810 can have an eyelet or other snap-type connector secured thereto.

Method of Making Biomedical Electrical Conductors

The biomedical electrical conductors of the present invention can be made by conventional coating techniques. Application of an ink containing electrically conductive component particles, an ink containing inorganic oxide particles, or a blended ink containing particles of both electrically conductive component and inorganic oxide, can employ screen printing or knife coating methods, followed by drying to evaporate solvent, e.g. water, from the ink applied. When knife coating is employed, a gap of about 25 to 100 μm is conventionally used, preferably about 50 μm. To minimize surface defects in the coating, a web speed of less than about 7 m/min. is possible with 2 m/min. preferred when coating is made on a substrate in a continuous process.

Drying of the ink on the nonconductive, polymeric film substrate so coated can take up to about 10 minutes at 145° C. heat to yield a thickness of about 10 to 15 μm. Alternatively, the drying can be conducted at about 150°–160° C. with a relatively high air velocity of about 0.8–4.6 m/secs above and below the substrate being coated. Preferably the drying occurs in two zones with the air velocity in the first zone ranging from about 1.4 to about 2.8 m/secs. above and below the substrate, with a web speed below about 2 m/min.

Coating of depolarizing inorganic oxide-based ink on that portion of the graphite layer intended to overlay an ionically conductive medium is followed by drying for about 10 minutes at about 40°–70° C. heat to yield a coated thickness of about 40–60 μm.

A slot fed knife is preferably used to coat the depolarizing inorganic oxide-based ink, where the slot width is preferably about 40–50 mm when the coating width is about 50–60 mm. Preferably the contact angle is about 0°. To minimize air entrainment in the coating, a web speed of less than about 5 m/min. is possible with 2 m/min. preferred when coating is made on a substrate in a continuous process.

Alternatively, drying of the depolarizing layer can be conducted at about 65°–75° C. with a relatively lower air velocity of about 0.1–1.2 m/secs. Preferably the drying occurs in two zones with the air velocity in the first zone ranging from about 1.4 to about 2.8 m/secs. above and below the substrate being coated, with the web speed during drying less than about 2 m/min.

After the biomedical electrical conductor is constructed, it can be used in assembly with other components disclosed in the electrode patents referenced above to make a variety of biomedical electrodes suited for a variety of purposes. Using an inexpensive, essentially x-ray transparent, thin, flexible, conformable biomedical electrical conductor of the present invention, one skilled in the art can replace more expensive, x-ray opaque silver/silver chloride conductors without losing the benefits of low-polarizing electrode performance.

The following test methods and examples further explain the scope of the present invention.

The Association for the Advancement of Medical Instrumentation (AAMI) has adopted the following standards and testing methods to determine proper performance for a biomedical electrode used for ECG Disposable Electrodes. See the "American National Standard for Pregelled ECG Disposable Electrodes" Association for the Advancement of Medical Instrumentation (1984), the disclosure of which is incorporated by reference, for testing methods and conditions for minimum standards for D.C. Offset (100 mV), A.C. Impedance (2 kOhms), and Defibrillation Overload Recovery (less than 100 mV 5 seconds after 4 capacitor discharges and a rate of change of residual polarization potential no greater than 1 mV/sec.)

EXAMPLES

Example 1

A coating composition was prepared by mixing 70 percent by weight of a graphite ink with a polyester binder commercially available as JEF-120 from Acheson Japan Co. of Kobe, Japan with 30 percent by weight of butyl carbitol acetate as a solvent, the solvent commercially available from Waco Co.

Example 2

A series of inks according to the present invention were prepared according to Table 1 below. All values are in weight percent.

TABLE 1

| Name | MnO2 | MC | KCl | Water | MA8 | EC | Denka |
|------|------|-----|-----|-------|-----|-----|-------|
| Ink A | 24.4 | 1.7 | 0.3 | 70.8 | 2.8 | | |
| Ink B | 21.8 | 1.7 | 0.3 | 70.8 | 5.4 | | |
| Ink C | 24.4 | 1.7 | 0.3 | 70.8 | | 2.8 | |
| Ink D | 24.4 | 1.7 | 0.3 | 70.8 | | | 2.8 |
| Ink E | 21.8 | 1.7 | 0.3 | 70.8 | | | 5.4 |

"MnO2" represents activated manganese dioxide commercially available from Johnson Matthey Co.

"MC" represents methyl cellulose commercially available as EM4000 from Matsumoto Chemical Co.

"MA8" represents carbon in the form of acidic furnace black commercially available from Mitsubishi Chemical Co.

"EC" represents carbon in the form of Ketjen black commercially available from Azko Chemical Co.

"Denka" represents carbon in the form of acetylene black commercially available from Denka Co.

All the inks were mixed in a high-shear mixer, and then vacuumed for the purpose of defoaming.

Example 3

A conductive adhesive was prepared according the the following formula. Values are in weight percent.

| | |
|---|---|
| Polyvinyl pyrrolidone (commercially available from BASF and crosslinked according to U.S. Pat. No. 5,276,079) | 13.2 |
| polyethylene glycol (commercially available as "PEG 300" from Union Carbide) | 26.0 |
| potassium chloride | 0.8 |
| water | 60.0 |

The components were mixed in a high shear mixer, then vacuumed for defoaming before coating.

Example 4

A conductive adhesive was prepared according the the following formula. Values are in weight percent.

| | |
|---|---|
| Cross-linked polyvinyl pyrollidone (commercially available from BASF and crosslinked according to U.S. Pat. No. 5,276,079) | 9.9 |
| polyethylene glycol (commercially available as "Peg 600" from Union Carbide) | 4.8 |
| polyethylene glycol methyl ether (commercially available as "Carbowax 550 from Union Carbide) | 14.7 |
| potassium chloride | 0.6 |
| water | 70.0 |

The components were mixed in a high shear mixer, then vacuumed for defoaming before coating.

Example 5

The ink of Example 1 was coated on a polymeric film in order to create a conductive layer. The polymeric film was a polyethylene terephthalate, 100 micrometers in thickness, commercially available as EMBLET T-100 film from Unitika Co. of Japan. The ink was applied with a laboratory knife coater with the knife-to-roll gap being set at 75 micrometers. The applied coatings were then dried at 145 degrees C. in a static drying oven for 6 minutes. The finished coating was about 12 micrometers in thickness.

Example 6

The inks of Example 2 were each coated on the polymeric film described in Example 5 in order to create thin, conformable depolarizing conductors. The inks were applied with a laboratory knife coater with the knife-to-roll gap being set at 100 micrometers. The applied coatings were then dried at 70 degrees C. in a static drying oven for 6 minutes. The finished coatings were between about 40 to 50 micrometers in thickness.

Example 7

The depolarizing conductors Example 6 were each coated with the conductive adhesive of Example 3 in order to create test sheets for evaluating properties. The adhesive was applied with a laboratory knife coater with the knife-to-roll gap being set at 800 micrometers. The applied coatings were then dried at 70 degrees C. in a static drying oven for 20 minutes. The finished coatings were between about 200 to 250 micrometers in thickness.

Example 8

The test sheets of Example 7 were evaluated for physical properties. In Table 2 below, Sheets A–E were prepared with Inks A–E, respectively. The wetting condition and surface condition were evaluated by visual inspection through the transparent conductive adhesive. The adhesion strength was evaluated by applying and then peeling the test sheet from human skin; breakage of the depolarizing layer was the criteria for unacceptable performance.

TABLE 2

| Sample Name | wetting condition | surface condition | adhesion strength |
|---|---|---|---|
| Sheet A | good | smooth | good |
| Sheet B | good | smooth | good |
| Sheet C | poor | rough | not good |
| Sheet D | poor | rough | good |
| Sheet E | poor | rough | good |

Example 9

In order to determine the dry-out properties to be expected of bioelectrodes according to the present invention, test sheets made according to Example 7, utilizing Ink A, but dried for varying lengths of time and evaluated for electrical properties according to the AAMI standards discussed above. Table 3 shows the results.

TABLE 3

| Drying time of adhesive (70° C.) | DC offset mV at 60 seconds | AC impedance ohms at 10 Hz | SDR of 4th pulse (offset) mV at 5 sec | (slope) mV/sec |
|---|---|---|---|---|
| 20 min. | 2.2 | 392 | 23.2 | −0.1 |
| 40 min. | 5.0 | 537 | 32.7 | −0.3 |
| 60 min. | 0.6 | 1957 | 52.6 | −1.2 |
| 90+ min. (to full dry out) | −0.1 | 4052 | 130.7 | −5.2 |

Example 10

In order to determine the effect of different depolarizing layers on dry-out properties of test sheets made from all the inks of Example 2 were made according to Example 9, except that all the test sheets were dried to dry-out. These were then evaluated for electrical properties as per Example 9. Table 4 shows the results.

TABLE 4

| Drying time of adhesive (70° C.) | DC offset mV at 60 seconds | AC imped- ance ohms at 10 Hz | SDR of 4th pulse (offset) mV at 5 sec | (slope) mV/sec |
| --- | --- | --- | --- | --- |
| Sheet A | −0.1 | 4052 | 130.7 | −5.2 |
| Sheet B | −6.3 | 616 | 33.8 | −0.3 |
| Sheet C | 3.1 | 607 | 25.6 | −0.6 |
| Sheet D | 2.4 | 585 | 51.7 | −0.6 |
| Sheet E | 14.2 | 408 | 57.0 | −0.3 |

Example 11

Because the several examples described above indicate a favorable mix of properties when Ink B was used with the present invention, an experiment was conducted to optimize and scale up the manufacture of an electrode incorporating this compound.

The coating composition of Example 1 was coated on the PET film discussed in Example 5 using a knife coater set to a knife gap of 80 micrometers and a coating speed of 1 meter/minute. The applied coating was then dried at 145 degrees C. in a 7.5 meter drying oven. The finished coating was about 12 micrometers in thickness.

This coated film was then coated with Ink B as described in Example 2, using a die coater set to a die space of 200 micrometers, a coating gap of 142 micrometers, and a die head angle of 0.1 degrees. The coating speed was 1 meter/minute, and the applied coating was then dried at 57 degrees C. in a 7.5 meter drying oven. The finished layer was about 35 micrometers in thickness.

This coated film was then coated with conductive adhesive as described in Example 4, using a die coater set to a die space of 500 micrometers, a coating gap of 1100 micrometers, and a die head angle of 0.1 degrees. The coating speed was 1 meter/minute, and the applied coating was then dried at 91 degrees C. in a 7.5 meter drying oven. The finished layer was about 200 micrometers in thickness.

This coated film was cut to a shape suitable for forming the electrode depicted in FIG. 1, using a die cutter. It was observed that there was no breakage of the coated layers at the cut edges after this operation. Some of the electrodes were applied to human skin, and a peel test was performed. No breakage of the coatings was observed following the peel test. An electrical test was performed according to the AAMI standards, yielding the following results as an average of 10 trials. Table 5 shows the results.

TABLE 5

| | DC offset mV at 60 seconds | AC imped- ance ohms at 10 Hz | SDR of 4th pulse (offset) mV at 5 sec | (slope) mV/sec |
| --- | --- | --- | --- | --- |
| Example 12 | 2.3 | 442 | 33.5 | −0.3 |
| AAMI minimum requirement | <100 | <2000 | <100 | <1.0 |

Example 12

A conductive adhesive was prepared according the the following formula. Values are in weight percent.

| | |
| --- | --- |
| Cross-linked polyvinyl pyrrolidone (commercially available from BASF and crosslinked according to U.S. Pat. No. 5,276,079) | 9.4 |
| polyethylene glycol methyl ether (PEGME) (commercially available as "Carbowax 550" from Union Carbide) | 18.6 |
| potassium chloride | 0.6 |
| water | 71.4 |

The KCl, water and PEGME were placed into a mixing vessel and mixed with a screw mixer until the salt was dissolved. The crosslinked polyvinylpyrrolidone was added to the vessel, and mixed until the polymer was dispersed.

Example 13

The conductive adhesive of Example 12 was coated on a polymeric film in order to test how adhesive properties vary with drying time. The polymeric film was a polyethylene terephthalate, 100 micrometers in thickness, commercially available as "EMBLET T-100" film from Unitika Co. of Japan, which had been lightly corona treated by Unitika Co. prior to delivery. The conductive adhesive was applied with a Konma brand roll coater with the knife-to-roll gap being set at 750 micrometers. The applied coatings were then dried at 65 degrees C. in a static drying oven for 20, 30, 40, 50, and 60 minutes. After drying, the coated film was covered with a liner and cut into 25 mm by 50 mm sample plates. Each sample plate was adhered to a standard Phenol plate and pressed down with a 1 kilogram roller twice. Each sample was then tested for 180 degree peel strength. After the peel test, finger tack was tested by a trial by hand, and the presence of any residue on the Phenol plate was noted. Tables 6–8 show the results.

TABLE 6

Peel test performed at 25 degrees C.

| Drying time (minutes) | Visual appearance | Finger tack | 180 degree strength (g) | Residue |
| --- | --- | --- | --- | --- |
| 20 | much water | strong | 7 | yes |
| 30 | soft, clear | strong | 30 | yes |
| 40 | hard, clear | very strong | 65 | no |
| 50 | partly hard, white | moderate | 320 | no |
| 60 | hard, white | weak | 55 | no |

TABLE 7

Peel test performed at 37 degrees C.

| Drying time (minutes) | Visual appearance | Finger tack | 180 degree strength (g) | residue |
| --- | --- | --- | --- | --- |
| 20 | much water | strong | 4 | yes |
| 30 | soft, clear | very strong | 40 | yes |
| 40 | hard, clear | very strong | 120 | no |
| 50 | hard, clear | strong | 185 | no |
| 60 | hard, clear | strong | 220 | yes |

TABLE 8

| | Peel test performed at 45 degrees C. | | | |
|---|---|---|---|---|
| Drying time (minutes) | Visual appearance | Finger tack | 180 degree strength (g) | residue |
| 30 | soft, clear | very strong | 31 | yes |
| 40 | hard, clear | very strong | 120 | no |
| 50 | hard, clear | very strong | 220 | yes |
| 60 | hard, clear | very strong | 320 | yes |

It is therefore to be noted that drying time for the conductive adhesive has an influence on the final properties of the assembled electrode, and must be optimized.

Example 14

A coating composition was prepared by mixing 70 per cent by weight of a graphite ink with a polyester binder commercially available as JEF-120 from Acheson Japan Co. of Kobe, Japan with 30 percent by weight of butyl carbitol acetate as a solvent, the solvent commercially available from Waco Co. Three percent by weight of the ink of a polyisocyanate cross-linking agent identified as Hardner commercially available from Acheson Japan Co. was added.

Example 15

The ink of Example 14 was coated on a polymeric film in order to create a conductive layer. The polymeric film was a polyethylene terephthalate, 100 micrometers in thickness, commercially available as EMBLET T-100 film from Unitika Co. of Japan, with which had been lightly corona treated by Unitika Co. prior to delivery. The ink was applied with a roll coater, and then the applied coating was then dried at 120 degrees C. The finished coating was about 13 micrometers in thickness.

Example 16

An ink was prepared according to the following formula. Values are in parts by weight.

| | |
|---|---|
| activated manganese dioxide (commercially available from J.M.) | 39.7 |
| polyvinyl alcohol (comercially available as Poval 2000 from Kishiwa Chemical Co.) | 0.8 |
| methyl cellulose (commercially availabe as Marpolose EM4000 from Matsumoto Chemical) | 0.8 |
| calcium chloride | 0.6 |
| water | 58.1 |

This ink was coated on the coated film of Example 15 in order to create depolarizing conductors. Before this coating step, some of the coated films from Example 15 were wiped with paper to modify the surface properties. The ink was then applied with a roll coater adjusted to several gap sizes. The applied coatings were then dried at 70 degrees C. in a static drying oven for 10 minutes, yielding several samples with layer thicknesses variously of 30, 35, and 45 micrometers, depending on the gap size.

Example 17

The depolarizing conductor of Example 16 was each coated with the conductive adhesive of Example 12 in order to create test samples for evaluating aging properties. The adhesive was applied with a roll coater and then dried. The conductors with their adhesive coatings were then tested for aging by being placed in an oven at 57 degrees C., and tested for adhesive properties each week for six weeks. Table 9 shows the results.

TABLE 9

| Conductive layer wiped? | Thickness of depolarizing layer | Week | | | | | |
|---|---|---|---|---|---|---|---|
| | | 1 | 2 | 3 | 4 | 5 | 6 |
| yes | 30 micrometers | OK | OK | OK | OK | OK | NG |
| yes | 35 | OK | OK | OK | OK | OK | NG |
| yes | 45 | OK | OK | OK | OK | OK | NG |
| no | 30 | OK | OK | OK | OK | OK | OK |
| no | 35 | OK | OK | OK | OK | OK | OK |
| no | 45 | OK | OK | OK | OK | OK | OK |

"NG" means not good.

Example 18

A conductive adhesive was prepared from a monomeric solution according to copending, coassigned U.S. patent application Ser. No. 08/188,269 (Attorney Docket 48237USA7A), now abandoned. The monomeric solution consisted of 71.25 g of Isooctyl Acrylate, 0.795 g of benzildimethylketal (commercially available as Irgacure 651 from Ciba Geigy), 12.31 g of acrylic acid, 16.60 g of a 4% KCl aqueous solution, 25.29 g of polyethylene glycol acrylate (750,000 M.W.), and 24.99 g of alkylene polyalkoxy sulfate surfactant (SAM 211 (K+) commercially available as from PPG Industries, Inc.). This monomeric solution was cured using ultraviolet light of 350 nm for sufficient time to provide about 680 mJ/cm$^2$ of energy between two silicone coated release liners (the upper release liner being a silicone coated polyester release liner). The resulting conductive adhesive was made into an electrode shown in FIG. 1 (having adhesive dimensions of 2.54 cm×2.54 cm) by lamination onto a piece of the conductor (having dimensions of 2.54 cm×3.175 cm) produced according to Example 11 above. A second electrode was similarly made. These two electrodes were then evaluated for electrical properties according to the AAMI standards discussed above at various time increments. Table 10 shows the results.

TABLE 10

| DC | AC | SDR of 3rd Pulse | |
|---|---|---|---|
| Offset mV | Impedence Ohms | (offset) mV | (slope) mV/s |
| −2.0 | 461 | @ 5 sec.   8.4 | — |
| | | @ 15 sec.  7.3 | −0.1 |
| | | @ 25 sec.  6.8 | −0.0 |
| | | @ 35 sec.  6.4 | −0.0 |

Example 19

Example 18 was repeated except that polyethylene glycol acrylate 750 was replaced with polyethylene glycol acrylate ester commercially available from Shin-Nakamura Chemical Co. of Wakayama, Japan. AAMI tests resulted in the following values with SDR measured at 5 secs. Table 11 shows the results.

TABLE 11

| DC Offset mV | AC Impedence Ohms | SDR of 3rd Pulse (offset) mV at 5 sec. | (slope) mV/s |
|---|---|---|---|
| 3.7 | 403 | 9.3 | −0.1 |

Example 20

Example 19 was repeated under an aging test by being placed in a moisture barrier pouch in an oven heated to 49° C. and removed for testing at 1, 2, 4, and 8 weeks. AAMI tests resulted in the following values with SDR measured at 5 secs. Table 12 shows the results.

TABLE 12

| Week | DC Offset mV | AC Impedance Ohms | SDR of 3rd Pulse (offset) mV | (slope) mV/s |
|---|---|---|---|---|
| 1 | 2.3 | 713 | 4.6 | −0.1 |
| 2 | −0.8 | 906 | 15.3 | −0.1 |
| 4 | −1.4 | 547 | 14.7 | −0.1 |
| 8 | −2.5 | 614 | 15.4 | −0.2 |

Examples 21 and 22

Two different conductor sheets were prepared using the same graphite ink formulations, the same polyester base film, but different depolarizing layer formulations. The base film was 75 μm polyethylene terephthalate film (Emblet T-75 film commercially available from Unitika Co. of Osaka, Japan), which was treated on the coating side by a corona discharge by Unitika Co. prior to delivery.

The graphite ink was prepared from JEF-120 branded graphite ink (commercially available from Acheson Japan Co. of Kobe, Japan) at 80 weight percent and butylacetate solvent at 20 weight percent.

The graphite ink and solvent were mixed by air mixer until in a well-mixed condition. After mixing, the mixture was filtered with two sheets of gauze cloth and stored.

The depolarizing layer was prepared by either of two formulae. In both formulae, an acrylic emulsion adhesive was added for strong adhesion, and an alkaline agent was added for dispersion stability. One used KOH as the alkaline agent; the other used $NH_3$ as the alkaline agent. The solid depolarizing layer by the Example 21 ink contained the active KOH of about 0.1 wt. %. The solid depolarizing layer of Example 22 contained no alkaline agent by the evaporation of $NH_3$. Their formulae are shown in Table 13.

TABLE 13

Formulae of $MnO_2$ ink or depolarizing layer

| Material | (wt. %) Example 21 | Example 22 |
|---|---|---|
| Electrolytic $MnO_2$ powder | 25.6 | 25.6 |
| MA8 Acidic Furnace carbon black | 6.4 | 6.4 |
| Methylcellulose binder stock | 28.8 | 28.8 |
| Acrylic emulsion adhesive | 7.0 | 7.0 |
| KCl | 0.13 | 0.13 |
| 1N—KOH | 9.6 | — |
| 25% ammonia water | — | 1.6 |
| Ion exchanged water | 22.47 | 30.47 |
| (Solid %) | (36.6) | (36.6) |

*Electrolytic $MnO_2$ powder: FMH—$MnO_2$ of Tosoh Co., Japan
*MA8 Acidic Furnace carbon black: Mitsubishi Chem Co., Japan
*Acrylic (Isooctyl acrylate/acrylic acid 95/5) emulsion prepared according to U.S. Pat. No. RE 24,906
*Methylcellulose binder stock: 2.3 wt. % solution of EM4000 Methyl cellulose: Matsumoto Chem Co., Japan The pH of the ink was 12 for the Example 21 ink and 11 for the Example 22 ink. The ink without binder stock or emulsion adhesive was mixed in the plastic can by air mixer and stored. Mixing occurred in the order of KCl, then carbon black, then $MnO_2$ powder, then alkaline agent. In order to keep dispersion stability of ink, the stored ink was mixed again before coating, and methylcellulose binder stock and acrylic emulsion adhesive were mixed into the stored ink by air mixer until well-mixed. The mixture was filtered by 2 sheets of gauze cloth and poured into the hopper of a Moyno pump, commercially available from Heishin Engineering and Equipment Co. of Kobe, Japan.

The pot life of the inks of Examples 21 and 22 were over 6 hours. The coating ink in the hopper was continually mixed by a mini mixer to minimize separation of the adhesive emulsion. For the Example 22 ink, the hopper was sealed to minimize evaporation of $NH_3$ from the ink.

The coating of graphite ink and $MnO_2$ ink were carried out according to the conditions identified in Table 14 for both Examples 21 and 22.

TABLE 14

| | Graphite Coating | $MnO_2$ Coating |
|---|---|---|
| Type of Substrate | PET | Graphite on PET |
| Substrate Thickness* $10^{-6}$ [m] | 75 | 86 |
| Coating Width [mm] | 135 | 54 |
| Coating Caliper* $10^{-6}$ [m] | 11 | 60 |
| Coating Condition | | |
| Type of Coater | Die (FB) | Die (SFK) |
| Slot Gap [mm] | 0.2 | 1 |
| Slot Width [mm] | 130 | 46 |
| CoatingSpeed [m/min.] | 2 | 2 |
| FB | | |
| Upstream Roll [mm] | 290 | |
| Downstream Roll [mm] | 521 | |
| SFK | | |
| Die to Web distance* $10^{-6}$ [m] | | 289 |
| Die Angle [degree] | | 0 |
| Type of Pump | Zenith | Moyno |
| Pump Size [cc/rev.] | 0.58 | 0.1 |
| Pump Speed [rpm] | 23 | 108 |
| Filter | Roki Techno Co., Ltd. SL-700 | |
| Tension [Kg/Substrate width] | | |
| Unwinder | 2 | 2 |
| Winder | 2 | 2 |
| Drying Condition | | |
| Blower Revolution [Hz] | | |
| Zone 1 Supply | 24 | 12 |

TABLE 14-continued

| | Graphite Coating | MnO$_2$ Coating |
|---|---|---|
| Zone 2 Supply | 18 | 9 |
| Exhaust | 55 | 55 |
| Recirculation | Y | N |
| Back Side Heating | N | Y |
| Oven Temperature [°C.] | | |
| Zone 1 Max | 154 | 71 |
| Zone 2 Min | 152 | 67 |
| Zone 2 Max | 159 | 72 |
| Zone 2 Min | 158 | 67 |

FB = Fluid Bearing Die
SFK = Slot Fed Knife Die

During processing, it was important to:

a) Use slot fed knife coating die head for MnO$_2$ ink coating without air entrainment;

b) Provide a drying condition for MnO$_2$ ink to keep smooth surface and strong adhesion on the graphite surface c) Use Moyno pump for MnO$_2$ ink d) Mix and seal mechanism on the hopper for MnO$_2$ ink e) Avoid use of MnO$_2$ ink which was stored for long time f) Filter the mixed ink before use The coated conductor sheets of Examples 21 and 22 were evaluated for physical properties and electrical properties. The coated graphite sheet was evaluated for thickness, coating weight and surface resistance. Table 15 shows the results.

TABLE 15

| Evaluation of the coated graphic sheet | |
|---|---|
| | Both Example 21 and Example 22 |
| Thickness (solid) | 11 to 12 μm |
| Coated weight (solid) | 0.204 g/10 cm$^2$ |
| Surface resistance | 40 to 50 Ω/sq. |

The coated MnO$_2$ layer was evaluated for coated weight, softness, edge break, delamination and electrical performance. As the coated surface was very rough, it was difficult to measure the coated thickness. So, the coated weight was measured. The softness was evaluated with the coated sheet bent 180° to determine how much of the depolarizing layer came of the graphite layer. The edge break was evaluated to determine if the depolarizing layer at the edge of electrode came off the graphite layer. The delamination was evaluated if the depolarizing layer was off from the graphite layer, when the conductive adhesive of the electrode was peeled off. The electrical performance was evaluated on the AAMI standards described above.

TABLE 16

| Evaluation of the coated depolarizing layer | | |
|---|---|---|
| | Example 21 | Example 22 |
| Coated weight (solid) | 0.987 g/100 cm$^2$ | 0.793 g/100 cm$^2$ |
| Softness | No off | No off |
| Edge Brak | No break | No break |
| Delamination | No | No |
| AAMI standards | Satisfied | Satisfied |

Examples 23A, 23B, 24A, and 24B

Two types of biomedical electrodes were fabricated with coated conductor sheets of Examples 21 and 22 and conductive adhesive backing electrode (EKG) film and liner film. One was in the form of FIGS. 1 and 2 and the other electrode (ECG) was in the form of FIGS. 3 and 4. For the electrode of FIGS. 1 and 2, five electrodes were adhered on the same liner sheet, and two sheets were packed in a moisture barrier pouch and stored. For the electrode of FIGS. 3 and 4, ten electrodes were adhered on the same liner sheet, and packed in a moisture barrier pouch and stored. The conductive adhesive used was a solid state conductive adhesive sheet made of polyurethane and LiClO$_4$ salts (commercially available as No.-VIII from TAKIRON Co., JAPAN). This adhesive was a special formulation conductive adhesive and contained less free polyole and had suitable tack for the skin adhesion.

Over 40 pouches for each kind of electrode were fabricated for the several evaluations including an aging study.

The fabricated electrodes were evaluated using AAMI standards, initial adhesive strength, and adhesion strength after 1 hour, trace quality and the delamination after peeling from the skin. AAMI standards were carried out as above. Adhesion strength was measured by 180° peeling test on the fore arm of an individual.

Table 17 shows the electrical performance on AAMI standards. All electrodes satisfied all AAMI standards.

TABLE 17

| | | Electrical performance on AAMI standards | | | |
|---|---|---|---|---|---|
| Ex. | Electrode | DC Offset (mV) @ 60 sec. | AC Impedance at 10 Hz (Ω) | SDR-4th Offset @ 5 sec (mV) | Pulse MAX Slope (mV/s) |
| 23A | ECG electrode (FIGS. 1 and 2) | −1.9 | 473 | 15.9 | −0.4 |
| | Example 21 conductor | −1.1 | 504 | 15.4 | −0.3 |
| | & TAKIRON VIII adhesive | 1.3 | 548 Ave. 508 | 21.3 | −0.5 Ave. −0.4 |
| 23B | EKG electrode (FIGS. 3 and 4) | 0.1 | 297 | 10.7 | −0.2 |
| | Example 21 conductor | 0.0 | 311 | 10.1 | −0.1 |
| | & TAKIRON VIII adhesive | 0.2 | 327 Ave. 312 | 10.8 | −0.2 Ave. −0.2 |
| 24A | ECG electrode (FIGS. 1 and 2) | −0.2 | 411 | 17.5 | −0.2 |
| | Example 22 conductor | −1.2 | 487 | 17.2 | −0.3 |

TABLE 17-continued

| | | Electrical performance on AAMl standards | | | |
|---|---|---|---|---|---|
| Ex. | Electrode | DC Offset (mV) @ 60 sec. | AC Impedance at 10 Hz (Ω) | SDR-4th Offset @ 5 sec (mV) | Pulse MAX Slope (mV/s) |
| | & TAKIRON VIII adhesive | −2.1 | 476 Ave. 458 | 16.5 | −0.3 Ave. −0.3 |
| 24B | EKG electrode (FIGS. 3 and 4) | −0.1 | 254 | 11.8 | −0.1 |
| | Example 22 conductor & TAKIRON VIII adhesive | 0.2 −0.4 | 279 302 Ave. 278 | 12.7 12.9 | −0.1 −0.2 Ave. −0.1 |

Table 18 shows the physical and clinical performance on skin adhesion strength, the delamination of $MnO_2$ depolarizing layer from the graphite layer, and trace quality of Lead(I).

TABLE 18

| | | Physical and clinical performance | | | |
|---|---|---|---|---|---|
| | | Skin adhesion Ave. (g) | | | |
| Ex. | Electrode | 180° initial | peel* @ 1 hour | Delamination | Trace form |
| 23A | ECG electrode Example 21 conductor & TAKIRON No. VIII | 218 | 170 | No | Good |
| 23B | EKG electrode Example 21 conductor & TAKIRON No. VIII | 60 | 133 | No | A little Base line Noise |
| 24A | ECG electrode Example 22 conductor & TAKIRON No. VIII | 308 | 305 | No | Good |
| 24B | EKG electrode Example 22 conductor & TAKIRON No. VIII | 94 | 183 | No | Good |

*Peeling speed: 0.3 m/min

Examples 23A, 23B, 24A, and 24B were repeated under an aging test by being placed in a moisture barrier pouch in an oven heated to 57° C. and removed for testing after 10 weeks. All sample electrodes satisfied the AAMI standards.

The embodiments and examples are illustrative of the invention. The scope of the invention is identified in the following claims and their equivalents.

What is claimed is:

1. A biomedical electrical conductor, comprising a multi-layered composite of a nonconductive film, an electrically conductive component in mechanical association with the nonconductive film and a thin, conformable layer of an inorganic oxide of low polarizability in mechanical association with at least a portion of the electrically conductive component, wherein the thin layer of inorganic oxide further comprises a binder relatively resistant to oxidation by the inorganic oxide.

2. The biomedical electrical conductor, according to claim 1, wherein the nonconductive film is a flexible polymeric film.

3. The biomedical electrical conductor, according to claim 2, wherein the electrically conductive component is essentially x-ray transparent and comprises a conductive polymer or a carbon-containing layer.

4. The biomedical electrical conductor, according to claim 3, wherein the inorganic oxide comprises manganese dioxide; wherein the binder comprises methyl cellulose; and wherein the carbon-containing layer comprises graphite.

5. The biomedical electrical conductor, according to claim 2, wherein the inorganic oxide comprises an oxide of manganese.

6. The biomedical electrical conductor, according to claim 5, wherein the oxide of manganese comprises manganese dioxide.

7. The biomedical electrical conductor, according to claim 1, wherein the binder is selected from the group consisting of a cellulose-containing water-soluble polymer, polyethylene oxide, poly(vinyl alcohol), poly(N-vinyl lactam), and combinations thereof.

8. The biomedical electrical conductor, according to claim 7, wherein the inorganic oxide comprises from about 0.01 to about 90 weight percent of the layer and wherein the binder comprises from about 0.01 to about 90 weight percent of the layer.

9. The biomedical electrical conductor, according to claim 7, wherein the inorganic oxide comprises manganese dioxide and wherein the binder comprises methyl cellulose.

10. The biomedical electrical conductor, according to claim 7 wherein the thin, conformable layer comprises an acrylic emulsion adhesive and an alkaline agent.

11. A biomedical electrode, comprising a biomedical electrical conductor and an ionically-conductive medium contacting the biomedical electrical conductor, wherein the biomedical electrical conductor comprises a multi-layered composite of a nonconductive film, an electrically conductive component in mechanical association with the nonconductive film and a thin, conformable layer of an inorganic oxide of low polarizability contacting the ionically-conductive medium and in mechanical association with at least a portion of the electrically conductive component, wherein the thin layer of inorganic oxide further comprises a binder relatively resistant to oxidation by the inorganic oxide.

12. The biomedical electrode according to claim 11, wherein the ionically-conductive medium comprises an ionically-conductive pressure sensitive adhesive.

13. The biomedical electrode according to claim 12, wherein the ionically-conductive pressure sensitive adhesion comprises an essentially nonvolatile plasticizer having hydroxy groups comprising less than about 3 percent of the molecular weight of the plasticizer.

14. The biomedical electrode according to claim 12, wherein the nonconductive film is a flexible polymeric film.

15. The biomedical electrode according to claim 14, wherein the electrically conductive component is essentially x-ray transparent and comprises a conductive polymer or a carbon-containing layer.

16. The biomedical electrode according to claim 15, wherein the inorganic oxide comprises manganese dioxide; wherein the binder comprises methyl cellulose and an acrylic emulsion adhesive; and wherein the carbon-containing layer comprises graphite.

17. The biomedical electrode according to claim 12, wherein the conductor comprises a tab portion and pad portion, and wherein the electrode further comprises an insulator construction having opposing sides contacting the conductor in a manner whereby the tab portion is positioned on one side of the insulator construction and the pad portion is positioned on an opposing side of the insulator construction.

18. The biomedical electrode according to claim 17, wherein the electrode further comprises a layer of skin adhesive on the opposing side contacting the pad portion and wherein the layer of skin adhesive includes a portion surrounding the layer of ionically conductive medium.

* * * * *